(12) United States Patent
Yamada et al.

(10) Patent No.: US 7,824,035 B2
(45) Date of Patent: Nov. 2, 2010

(54) OPHTHALMIC PHOTOGRAPHING APPARATUS

(75) Inventors: Yoshiyuki Yamada, Toyokawa (JP); Yuji Murase, Gamagori (JP); Mitsuo Yamamoto, Gamagori (JP); Yukihiro Higuchi, Gamagori (JP); Norimasa Satake, Aichi-ken (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 12/457,160

(22) Filed: Jun. 2, 2009

(65) Prior Publication Data

US 2009/0303438 A1 Dec. 10, 2009

(30) Foreign Application Priority Data

Jun. 2, 2008 (JP) ............................. 2008-145160
Jun. 2, 2008 (JP) ............................. 2008-145161

(51) Int. Cl.
*A61B 3/14* (2006.01)
(52) U.S. Cl. ...................................... 351/206; 351/210
(58) Field of Classification Search ................. 351/206, 351/208, 210, 216, 221, 223, 243
See application file for complete search history.

(56) References Cited

U.S. PATENT DOCUMENTS 4,899,194 A 2/1990 Hori 7,510,282 B2 3/2009 Ueno et al.

FOREIGN PATENT DOCUMENTS

| EP | 1 882 445 A2 | 1/2008 |
|---|---|---|
| JP | A-2005-279121 | 10/2005 |
| JP | A-2006-212153 | 8/2006 |
| JP | A-2008-29467 | 2/2008 |

*Primary Examiner*—Ricky L Mack
*Assistant Examiner*—Brandi N Thomas
(74) *Attorney, Agent, or Firm*—Oliff & Berridge, PLC

(57) ABSTRACT

An ophthalmic photographing apparatus comprising a photographing optical system for obtaining a regional image of an examinee's eye, comprising a light source, a focusing optical element movable in an optical-axis direction by a driving mechanism, and a photodetector, and a control unit controlling driving of the mechanism and obtain the image based on a signal from the photodetector, wherein the control unit further moves the optical element in predetermined steps/continuously to obtain the image at each position, calculates frequency distribution of luminance of each of the images to detect a change characteristic of luminance values having frequencies equal or exceeding a threshold value in the frequency distribution with respect to the optical element position, and detects a focus position of the optical element based on the change characteristics to move the optical element to a position corresponding to the detected focus position.

6 Claims, 4 Drawing Sheets

US 7,824,035 B2

OPHTHALMIC PHOTOGRAPHING APPARATUS

BACKGROUND OF THE INVENTION

1. Field of the Invention

The present invention relates to an ophthalmic photographing apparatus arranged to photograph an image of a predetermined region of an examinee's eye.

2. Description of Related Art

Conventionally, as an ophthalmic photographing apparatus arranged to photograph an image of an examinee's eye, there are known an optical coherence tomograph (OCT) for obtaining a tomographic image of an examinee's eye using low coherent light, a scanning laser ophthalmoscope (SLO) for obtaining a front image of an examinee's eye by scanning laser light on a fundus of the eye, a fundus camera for obtaining a front image of a fundus of an examinee's eye with the use of a two-dimensional image-pickup element by illuminating the whole of the fundus at a time, and other devices (see Japanese Patent application Unexamined Publication No. 2006-212153).

For example, for the fundus camera, a fundus camera including a target projection optical system is known, which is arranged to project a focus target onto a fundus of an examinee's eye and based on a photo-receiving signal at the time of photo-receiving reflection light of the focus target with the use of a photodetector, detect a focus state to automatically perform focus adjustment.

However, in the case of the OCT or SLO, it is difficult to include in its optical system a target projection optical system as used in the fundus camera, so that manual focus adjustment needs to be performed, which is time-consuming and troublesome for an examiner. In addition, even in the case of the fundus camera, including the target projection optical system in its optical system complicates the structure of the apparatus.

SUMMARY OF THE INVENTION

An object of the invention is to overcome the problems described above and to provide an ophthalmic photographing apparatus which is simple in structure, and is capable of performing appropriate focus adjustment.

To achieve the objects and in accordance with the purpose of the present invention, an ophthalmic photographing apparatus comprises a photographing optical system arranged to obtain an image of a given region of an examinee's eye, which comprises a light source arranged to illuminate the given region, a focusing optical element provided movable in a direction of an optical axis by a driving mechanism, and a photodetector arranged to photo-receive reflection light from the given region, and a control unit arranged to control driving of the driving mechanism, and obtain the image based on a signal outputted from the photodetector, wherein the control unit is arranged to further move the focusing optical element in predetermined steps or continuously to obtain the image at each position, calculate frequency distribution of luminance of each of the images to detect a change characteristic of luminance values having frequencies equal or exceeding a predetermined threshold value in the frequency distribution with respect to the position of the focusing optical element, and detect a focus position of the focusing optical element based on the change characteristics to move the focusing optical element to a position corresponding to the detected focus position.

Additional objects and advantages of the invention are set forth in the description which follows, are obvious from the description, or may be learned by practicing the invention. The objects and advantages of the invention may be realized and attained by the ophthalmic photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
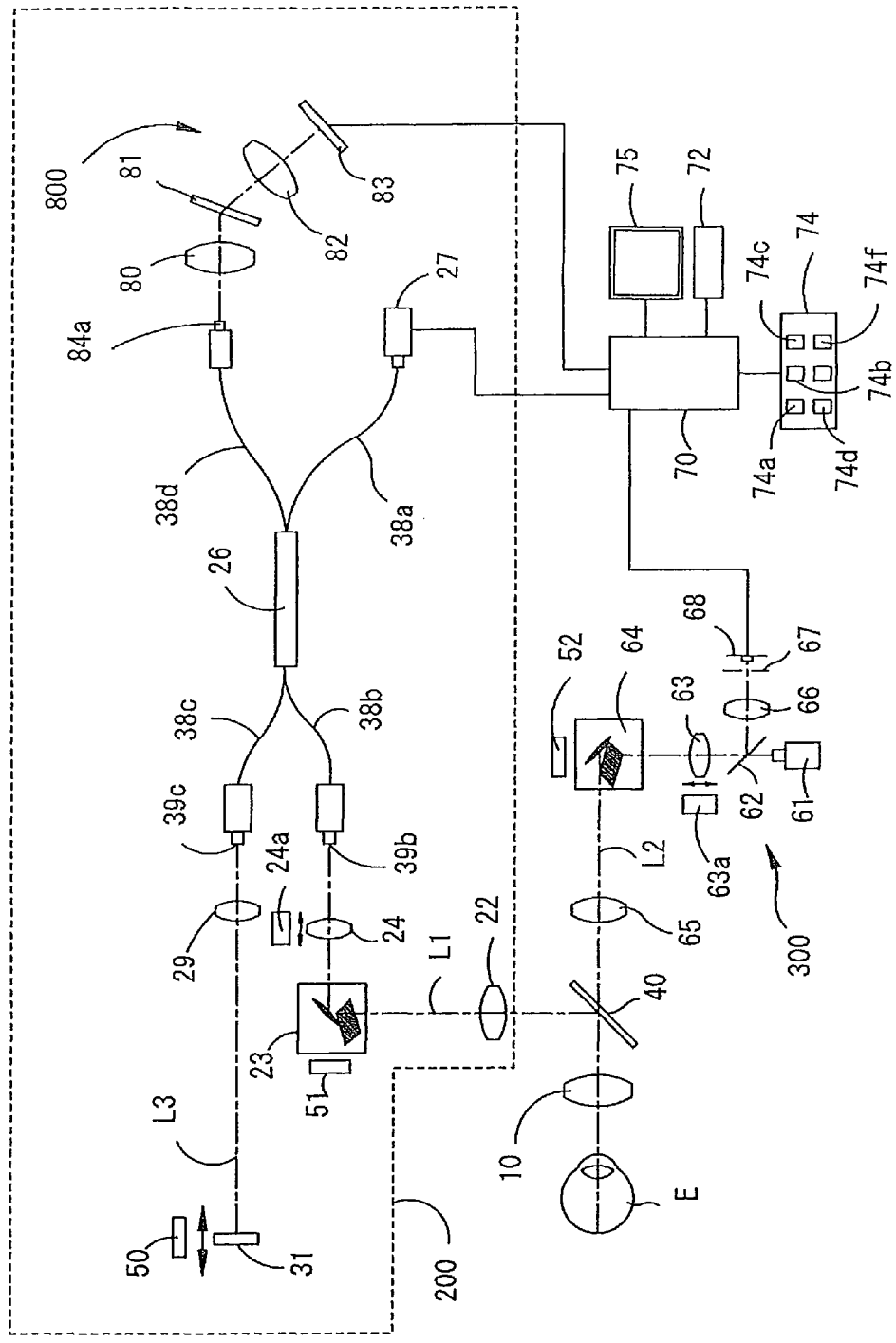
FIG. 1 is a view showing a schematic configuration of an optical system and a control system of an ophthalmic photographing apparatus according to a preferred embodiment of the present invention.

A detailed description of an ophthalmic photographing apparatus according to preferred embodiments of the present invention will now be provided with reference to the accompanying drawings. FIG. 1 is a view showing a schematic configuration of an optical system and a control system of the ophthalmic photographing apparatus according to one of the preferred embodiments of the present invention. Hereinafter, as one example of the ophthalmic photographing apparatus, a fundus-photographing apparatus arranged to photograph a fundus of an examinee's eye is explained. In addition, a depth direction of an examinee's eye E is referred to as a Z-direction (a direction of an optical axis L1), a horizontal direction is referred to as an X-direction, and a vertical direction is referred to as a Y-direction.

In FIG. 1, the optical system is roughly divided into an interference optical system (hereinafter, referred to as an OCT optical system) 200 arranged to obtain a tomographic image of a fundus of the eye E by an interferometric technique in a non-invasive method, and a scanning laser ophthalmoscope optical system (hereinafter, referred to as an SLO optical system) 300 arranged to obtain an SLO fundus image for observation by illuminating the fundus with infrared light.

A dichroic mirror 40 defines a light-dividing member, and has a property of reflecting measurement light (e.g., light with wavelengths in the vicinity of 840 nm) which is emitted from a measurement light source 27 of the OCT optical system 200, and a property of transmitting laser light (light different from the light source 27, e.g., light with wavelengths in the vicinity of 780 nm) which is emitted from an SLO light source 61 of the SLO optical system 300. In this case, the dichroic mirror 40 makes the optical axis L1 of the OCT optical system 200 coaxial with an optical axis L2 of the SLO optical system 300.

Firstly, a description of the OCT optical system 200 which is disposed at a reflection side of the dichroic mirror 40 is provided. The light source 27 is an OCT light source which emits low coherent light to be used as measurement light and reference light of the OCT optical system 200, and as the light source 27, an SLD light source is preferably used. Specifically, a light source having a center wavelength of 840 nm and a bandwidth of 50 nm is used. A fiber coupler 26 functions as both a light dividing member and a light synthesizing member. The light from the OCT light source 27 passes through an optical fiber 38a that functions as a light guide, and is divided into the reference light and the measurement light by the fiber coupler 26. The measurement light passes through an optical fiber 38b, and heads for the eye E. The reference light passes through an optical fiber 38c, and heads for a reference mirror 31.

On an optical path where the measurement light travels to the eye E, an end portion 39b of the optical fiber 38b from which the measurement light exits, a focusing lens 24 which is movable in an optical axis direction in accordance with refractive error of the eye E, a scanning unit 23 which is made up of two galvano mirrors in combination capable of scanning the measurement light in the X- and Y-directions on the fundus by driving of a scanning driving mechanism 51, and a relay lens 22 are disposed. The dichroic mirror 40 and an objective lens 10 function as a light guiding optical system arranged to guide the OCT measurement light from the OCT optical system 200 to the fundus. It is to be noted that, in the scanning unit 23 according to the preferred embodiment of the present invention, scanning directions of the measurement light scanned on the fundus can be arbitrarily set by arbitrarily adjusting reflection angles of the measurement light by using the two galvano mirrors. Thus, a tomographic image in a given region of the fundus can be obtained. Besides, the end portion 39b of the optical fiber 38b is disposed so as to be conjugate with the fundus, and the two galvano mirrors of the scanning unit 23 are disposed at positions substantially conjugate with a pupil of the eye E.

The measurement light reflected from the fundus passes through the objective lens 10, is reflected by the dichroic mirror 40, and heads for the OCT optical system 200, where the measurement light enters the end portion 39b of the optical fiber 38b via the relay lens 22, the two galvano mirrors of the scanning unit 23, and the focusing lens 24. The measurement light which enters the end portion 39b reaches an end portion 84a of an optical fiber 38d via the optical fiber 38b, the fiber coupler 26, and the optical fiber 38d.

Meanwhile, on an optical path where the reference light travels to the reference mirror 31, an end portion 39c of the optical fiber 38c from which the reference light exits, a collimator lens 29, and the reference mirror 31 are disposed. The reference mirror 31 is movable in an optical axis direction by a reference-mirror driving unit 50 in order to vary an optical path length of the reference light.

The reference light which is thus produced from the light emitted from the light source 27, and the reflection light from the fundus which is produced from the measurement light with which the fundus is illuminated are synthesized by the fiber coupler 26 to be made into interference light. Then, after passing through the optical fiber 38d, the interference light exits from the end portion 84a of the fiber 38d. A spectral optical system (a spectrometer unit) 800 arranged to disperse the interference light into frequency components in order to obtain an interference signal for each of the frequencies comprises a collimator lens 80, a grating mirror (a diffraction grating) 81, a condenser lens 82, and a photodetector 83. For the photodetector 83, a one-dimensional detector (a line sensor) which has sensitivity to an infrared range is used.

To be specific, the interference light exiting from the end portion 84a is made into parallel light by the collimator lens 80, and then is dispersed into the frequency components by the grating mirror 81. The interference light dispersed into the frequency components is collected on a photo-receiving surface of the photodetector 83 via the condenser lens 82. Thus, spectral information on interference fringes is recorded at the photodetector 83. Then, the spectral information is inputted into a calculation and control unit 70, and is analyzed by performing a Fourier transform thereon, whereby information on the eye E in the depth direction can be obtained. At this time, the calculation and control unit 70 can obtain the tomographic image by controlling the scanning unit 23 to scan the measurement light in a predetermined traverse direction on the fundus. For example, scanning the measurement light in the X- or Y-direction allows the tomographic image of the fundus on an X-Z or Y-Z plane to be obtained (in the present preferred embodiment of the present invention, a mode of thus obtaining the tomographic image by one-dimensionally scanning the measurement light on the fundus is referred to as B-scan). The obtained tomographic image is stored in a memory 72 connected to the calculation and control unit 70. It is also possible to obtain a three-dimensional image of the fundus by two-dimensionally scanning the measurement light in the X- and Y-directions. The obtainment of the OCT image in the present preferred embodiment of the present invention is made with the use of the two galvano mirrors of the scanning unit 23.

Next, a description of the SLO optical system (a confocal optical system) 300 which is disposed at a transmission side of the dichroic mirror 40 is provided. The SLO optical system 300 is roughly divided into an illumination optical system arranged to illuminate the fundus, and a photo-receiving optical system arranged to photo-receive reflection light from the fundus illuminated by the illumination optical system with the use of a photodetector, and is arranged to obtain a front image of the fundus based on a photo-receiving signal outputted from the photodetector. The light source 61 emits high coherent light and as the light source 61, an LD (Laser Diode) is preferably used. The laser light from the light source 61 is transmitted through a beam splitter 62 and a focusing lens 63 which is movable in a direction of the optical axis L2 in accordance with the refractive error of the eye E, is reflected by a scanning unit 64 which is made up of a galvano mirror oscillated by a driving unit 52 and a polygon mirror rotated by the driving unit 52, is transmitted through a relay lens 65, the dichroic mirror 40 and the objective lens 10, and is projected onto the fundus of the eye E to be collected thereon. The scanning unit 64 (the galvano mirror and the polygon mirror) is disposed at a position substantially conjugate with the pupil of the eye E. The scanning unit 64 is not limited to the above-described type, and a known scanning unit may be used.

The beam splitter 62 is disposed between the SLO light source 61 and the focusing lens 63. At a reflection side of the beam splitter 62, a condenser lens 66, a confocal opening 67 disposed at a position conjugate with the fundus, and a photodetector 68 for an SLO are disposed to constitute a confocal optical system.

The laser light reflected from the fundus passes through the objective lens 10, the relay lens 65, the galvano mirror and the polygon mirror of the scanning unit 64, and the focusing lens 63, and is reflected by the beam splitter 62. After collected by the condenser lens 66, the laser light is detected by the photodetector 68 via the confocal opening 67. Then, a photo-receiving signal detected by the photodetector 68 is inputted into the calculation and control unit 70 and based on the photo-receiving signal, the calculation and control unit 70 obtains a front image of the fundus. The obtained front image is stored in the memory 72. The obtainment of the SLO image is made by scanning the laser beam in the vertical direction (auxiliary scan) with the use of the galvano mirror of the scanning unit 64, and scanning the laser beam in the horizontal direction (main scan) with the use of the polygon mirror of the scanning unit 64.

The calculation and control unit 70 is connected with a display monitor 75 to control an image to be displayed. In addition, the calculation and control unit 70 is connected with the memory 72, a measurement starting switch 74a, a measurement position setting switch 74b, a photographing starting switch 74c, an automatic coherence switch 74d, an autofocus starting switch 74f, the driving unit 50, a first driving unit 63a arranged to move the focusing lens 63 in the optical axis direction, a second driving unit 24a arranged to move the focusing lens 24 in the optical axis direction, and other members.

Figure 2:
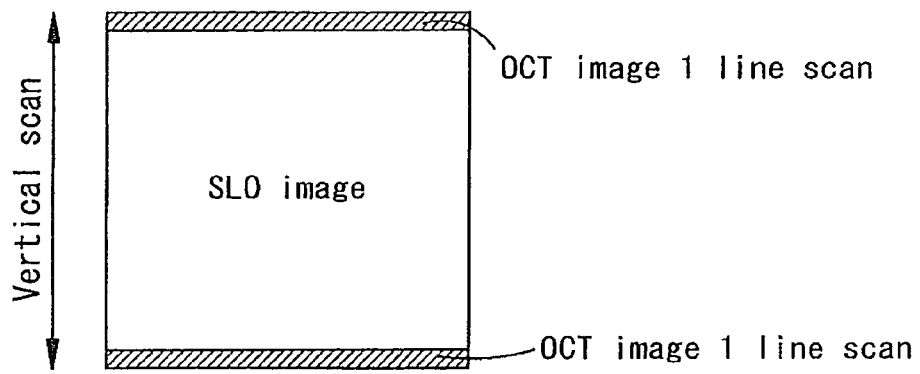
FIG. 2 is a view for illustrating the operation of the apparatus at the time of photographing an OCT image, and an SLO image (left side) in succession.

Next, a description of a manner of obtaining the tomographic image on the X-Z plane by the B-scan (a B-scan image) is provided. FIG. 2 is a view for illustrating the operation of the apparatus at the time of obtaining the OCT image and the SLO image (left side) in succession. The calculation and control unit 70 makes changeover of the irradiation light with which the fundus is irradiated in order to obtain the image of the fundus between the measurement light applied via the OCT optical system 200 and the laser light applied via the SLO optical system 300 by turning on and off the OCT light source 27 and the SLO light source 61 alternately. Accordingly, the interference signals detected by the photodetector 83 disposed in the OCT optical system 200, and the photo-receiving signals detected by the photodetector 68 disposed in the SLO optical system 300 are inputted into the calculation and control unit 70 in succession.

A description of the operation of the apparatus having the above-described configuration is provided. In this operation, the calculation and control unit 70 drives and controls the OCT optical system 200 and the SLO optical system 300 to keep obtaining an OCT image and an SLO image frame by frame, and controls the monitor 75 to always renew the OCT image and the SLO image displayed thereon. A scanning position (e.g., the X-direction) with reference to a center position of the SLO image is set as a position at which a first OCT image is to be obtained and which is not set by an examiner.

First, the examiner instructs the examinee to gaze at a fixation lamp (unillustrated), and performs alignment of the apparatus using a joystick (unillustrated) such that the measurement optical axis L1 is placed at a pupil center of the examinee's eye E while observing an anterior-segment observation image of the eye E which is picked up by an anterior-segment observation camera (unillustrated) on the monitor 75. The alignment with respect to the eye is thus completed, and the front image (SLO fundus image) of the fundus by the SLO optical system 300 is accordingly obtained and the SLO fundus image shows up on the monitor 75.

Next, the examiner pushes the autofocus starting switch 74f mounted on a control unit 74. When an operation signal is emitted from the autofocus starting switch 74f, the calculation and control unit 70 emits a trigger signal of starting autofocus control to start autofocus with respect to the SLO fundus image.

At this time, the calculation and control unit 70 subjects image data on the SLO fundus image obtained from the photo-receiving signal outputted from the photodetector 68 to differential processing and based on a result of the differential processing, obtains information for a differential histogram. In other words, the calculation and control unit 70 applies a filter for edge extraction (e.g., Laplacian transform, SOBEL) to the image data on the SLO fundus image to transform the image data into an edge image, and then plots a histogram of the edge image.

Figure 3:
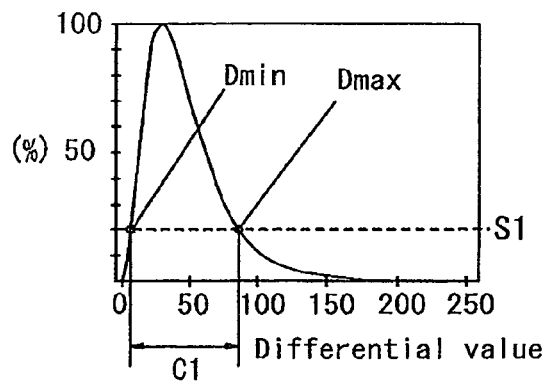
FIG. 3 is one example of a differential histogram obtained by subjecting an image signal of an SLO fundus image by an SLO optical system to differential processing.

FIG. 3 is one example of the differential histogram obtained by subjecting the image signal of the SLO fundus image to the differential processing. In FIG. 3, the horizontal axis indicates absolute values of differentiation (hereinafter, referred to as a differential value) d (d=1, 2, . . . 254), and the vertical axis indicates the numbers of pixels at the respectively corresponding differential values H(d), where the numbers are expressed as a percentage (%) by being normalized by the number of pixels at a peak differential value H(dp), ((H(d)/H(dp)). Besides, in the histogram in FIG. 3, data at the two end points (d=0, d=255) are omitted, and the differential values d are luminance values in the edge image which are expressed in a 255-step gradation.

At this time, the calculation and control unit 70 performs a calculation of an evaluation value of an image-formation state (a focus state) of the SLO fundus image by using the maximum value among the luminance values (the differential values) which have the pixel numbers of a predetermined percentage or more in the whole image in the histogram information. For example, as an evaluation value C1 of an image-formation state to be used for evaluating the image-formation state of the SLO fundus image, a difference between a maximum value Dmax and a minimum value Dmin among the differential values which are equal or exceed a threshold value S1 (e.g., 20%) in the differential histogram is obtained (C1=Dmax−Dmin). Besides, the threshold value S1 is set at a value such that the evaluation value C1 susceptibly varies in response to the change in the image-formation state of the SLO fundus image while preventing an influence of noise. The reason why the threshold value S1 is set at 20% in the present preferred embodiment of the present invention is to detect with high precision the change in an acute angle of an edge at a blood vessel region of the fundus which occupies a smaller range in the whole SLO fundus image. It is also preferable that only the maximum value Dmax among the differential values which are equal or exceed the threshold value S1 is set as the evaluation value C1 of the image-formation state. Yet, it is also preferable that the area of a region of the pixel numbers which are equal or exceed the threshold value S1 in the differential histogram (i.e., the area of a triangle whose base is the difference C1 between the maximum value Dmax and the minimum value Dmin) is used.

The evaluation value C1 of the image-formation state is high when the focusing lens 63 is in a focus position (i.e., when the SLO fundus image is in focus), and becomes gradually lower as the focusing lens 63 deviates from the focus position, so that the evaluation value C1 can be used for determining the focus state (the image-formation state) of the SLO fundus image.

At this time, the calculation and control unit 70 samples evaluation values C1 while moving the position of the focusing lens 63 disposed in the photo-receiving optical system of the SLO optical system 300, determines focus states based on a result of the sampling, and moves the focusing lens 63 to the focus position.

For example, in order to search an appropriate focus position, the calculation and control unit 70 drives and controls the driving unit 63a to move the focusing lens 63 to a plurality of travel positions which are set discretely in a movable range of the focusing lens 63, and obtains SLO fundus images at the travel positions. Then, the calculation and control unit 70 plots a differential histogram of each of the images obtained at the travel positions, and performs calculations of evaluation values C1. In this case, the calculation and control unit 70 may move the focusing lens 63 continuously, and perform the calculations of the evaluation values C1 continuously.

Figure 4:
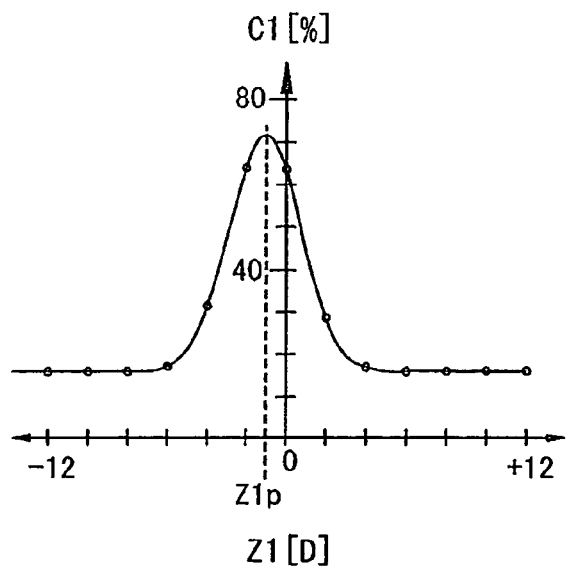
FIG. 4 is one example of a graph which presents a relation between evaluation values C1 of image-formation states and travel positions Z1 of a focusing lens.

FIG. 4 is one example of a graph which presents a relation between the evaluation values C1 and travel positions Z1 of the focusing lens 63. In FIG. 4, the relation is presented such that the focusing lens 63 is moved in a plus direction in steps of 2 D from a position corresponding to −12 D, and the evaluation values C1 are obtained in sequence until the focusing lens 63 is moved to a position corresponding to +12 D.

When the evaluation values C1 at the travel positions are obtained as described above, characteristics of the travel positions Z1 and the evaluation values C1 which are obtained discretely are subjected to interpolation to detect a focus position of the SLO optical system 300. For example, curve approximation is applied to the characteristics using such a function as have its maximum value in a moving range of the focusing lens 63, and a travel position $Z1p$ where the maximum evaluation value C1 is obtained in that curved line is obtained as information on the focus position of the SLO optical system 300. Examples of the manner of detecting the focus position by using the above-described interpolation include a manner using functional approximation, a manner using calculation of a barycenter, and a manner using calculation of an average value.

Next, the calculation and control unit 70 drives and controls the driving unit 63a to move the focusing lens 63 to a travel position corresponding to the thus-obtained focus position information, whereby the focus adjustment with respect to the SLO fundus image is completed.

Besides, in the case of sampling the evaluation values C1 as described above, it is also preferable that the movement of the focusing lens 63 is stopped when the curved line of the evaluation values C1 shifts from increase to decline.

Next, the calculation and control unit 70 obtains the above-described travel position of the focusing lens 63 by the autofocus control with respect to the SLO fundus image as information on a focus position of the OCT optical system 200 and based on the obtained focus position information, drives and controls the driving unit 24a to move the focusing lens 24 to the vicinity of its focus position.

For example, if the focus position of the SLO optical system 300 is a position corresponding to −3 D, the calculation and control unit 70 controls the OCT optical system 200 such that also the focus position of the OCT optical system 200 is brought to a position corresponding to −3 D. For this purpose, associations on a diopter basis are preestablished between the travel positions of the focusing lens 63 and the travel positions of the focusing lens 24 so that the focus position of the OCT optical system 200 can be set at a focus position corresponding to the focus position of the SLO optical system 300.

When the focusing lens 24 of the OCT optical system 200 is thus moved to a travel position corresponding to the focus position of the SLO optical system 300, the focusing lens 24 is moved to the vicinity of its focus position, so that the fundus reflection light which enters the end portion 39b increases.

After moving the focusing lens 24 to the vicinity of its focus position, the calculation and control unit 70 controls the reference mirror 31 which functions as an optical-path-length variable optical element and is disposed in the OCT optical system 200, to move based on the tomographic image obtained by the OCT optical system 200, and performs automatic adjustment of the optical path length. In this case, when the optical path length of the reference light and an optical path length of the measurement light become almost equal, the interference signals outputted from the photodetector 83 become obtainable as the tomographic image of the fundus (hereinafter, referred to as the OCT fundus image).

Figure 5:
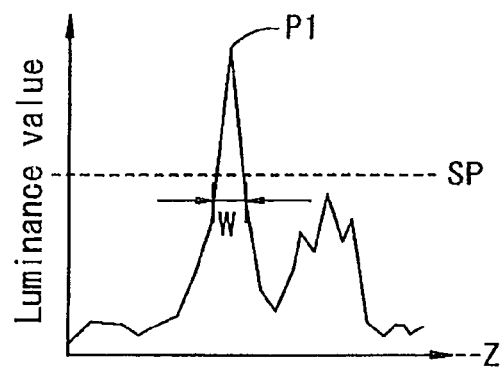
FIG. 5 is a view showing luminance distribution in a depth direction of the OCT image.

To be specific, after the completion of the rough autofocus control, the calculation and control unit 70 drives and controls the driving unit 50 to move the reference mirror 31 in the optical axis direction to vary the optical path length of the reference light until the OCT fundus image is obtained. FIG. 5 is a view showing luminance distribution in the depth direction of the OCT image.

At this time, while moving the reference mirror 31 in the optical axis direction, the calculation and control unit 70 detects a peak value P1 from luminance values in the depth direction in the OCT image obtained based on the interference signals from the photodetector 83, and based on whether or not the peak value P1 exceeds a predetermined threshold SP, determines whether or not the OCT fundus image is obtained.

Then, when the peak value P1 exceeds the predetermined threshold SP, the calculation and control unit 70 determines that the OCT fundus image is obtained, and determines whether the OCT fundus image is a real image or a virtual image. When a width W at a half value of the peak value P1 is smaller than a predetermined allowable width, the OCT fundus image is determined as a real image. Although the determination whether the OCT fundus image is a real image or a virtual image is made based on the width W at the half value in the above description, it is also preferable that the determination whether the OCT fundus image is a real image or a virtual image is made based on the sequence of the obtainment of real images and virtual images of the OCT fundus images which are obtained in succession when the optical path length is varied.

Figure 6:
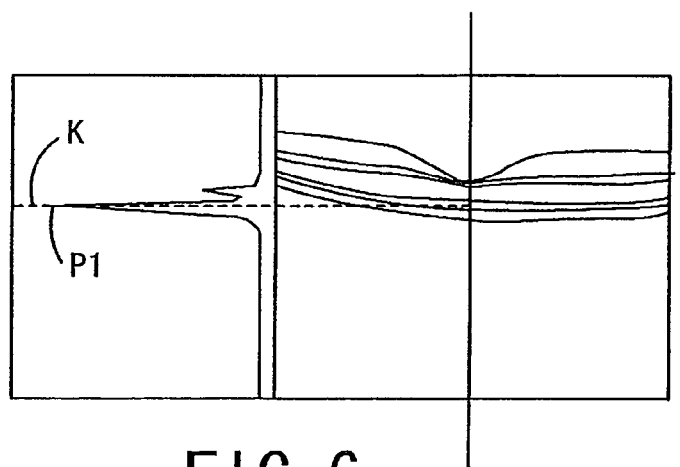
FIG. 6 is a view in which an image position of an OCT fundus image displayed on a monitor is adjusted.

Then, determining that a real image is obtained, the calculation and control unit 70 takes the position where the peak value P1 is detected from the luminance distribution in the depth direction as an image position as shown in FIG. 6, performs a calculation of a deviation amount between a predetermined optical-path-length adjustment position (see the broken line K in FIG. 6) and the image position, and moves the reference mirror 31 so as to eliminate the deviation amount.

When the adjustment of the optical path length is made as described above, the OCT fundus image is displayed on the monitor 75 together with the SLO fundus image. Then, the calculation and control unit 70 obtains information on the focus position of the OCT optical system 200 based on the OCT fundus image obtained by the OCT optical system 200, and moves the focusing lens 24 to the focus position.

Figure 7:
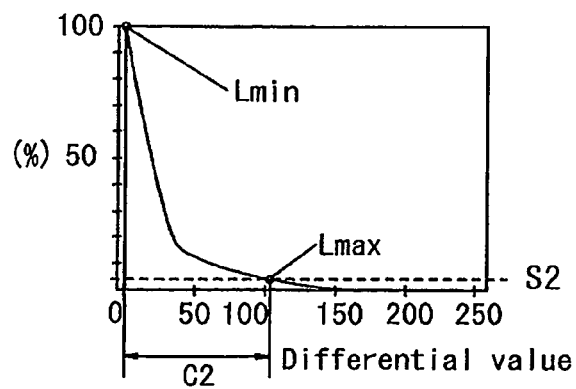
FIG. 7 is one example of a histogram based on an image signal of the OCT fundus image by an OCT optical system.

To be specific, the calculation and control unit 70 obtains information for a histogram of the OCT fundus image obtained by the OCT optical system 200. FIG. 7 is one example of the histogram based on an image signal of the OCT fundus image by the OCT optical system 200. In FIG. 7, the horizontal axis indicates luminance values k (k=1, 2, ... 254), and the vertical axis indicates the numbers of pixels at the respective luminance values H(k), where the numbers are expressed as a percentage (%) by being normalized by the number of pixels at a peak luminance value H(kp), ((H(k)/H(kp)). Besides, in the histogram in FIG. 7, data at the two end points (k=0, k=255) are omitted.

At this time, the calculation and control unit 70 performs a calculation of an evaluation value of an image-formation state (a focus state) of the OCT fundus image by using the maximum value among the luminance values which have the pixel numbers of a predetermined percentage or more in the whole image in the histogram information. For example, as an evaluation value C2 of an image-formation state to be used for evaluating the image-formation state of the OCT fundus image, a difference between a maximum value Lmax and a minimum value Lmin among the luminance values which are equal or exceed a threshold value S2 (e.g., 5%) in the histogram is obtained (C2=Lmax−Lmin). Besides, the threshold value S2 is preferably set at a value such that the evaluation value C2 susceptibly varies in response to the change in the image-formation state of the OCT fundus image while preventing an influence of noise. The reason why the threshold value S2 is set at 5% in the present preferred embodiment of the present invention is to detect with high precision the change of luminance value in a portion where the luminance value greatly changes in accordance with the change of a focus position in the whole OCT fundus image (especially, in a region corresponding to a neuroepithelial layer of retina in the OCT fundus image). It is also preferable that only the maximum value Lmax among the luminance values which are equal or exceed the threshold value S2 (e.g., 5%) is set as the evaluation value C2 of the image-formation state. Yet, it is also preferable that the area of a region of the pixel numbers which are equal or exceed the threshold value S2 in the histogram (i.e., the area of a triangle whose base is the difference C2 between the maximum value Lmax and the minimum value Lmin) is used.

The evaluation value C2 of the image-formation state is high when the focusing lens 24 is in the focus position (i.e., when the OCT fundus image is in focus), and becomes gradually lower as the focusing lens 24 deviates from the focus position, so that the evaluation value C2 can be used for determining the focus state (the image-formation state) of the OCT fundus image.

At this time, the calculation and control unit 70 samples evaluation values C2 while moving the position of the focusing lens 24 disposed in the photo-receiving optical system of the OCT optical system 200, determines focus states based on a result of the sampling, and moves the focusing lens 24 to the focus position.

For example, in order to search an appropriate focus position of the OCT fundus image, the calculation and control unit 70 drives and controls the driving unit 24a, and obtains an OCT fundus image at each travel position. Then, the calculation and control unit 70 plots a histogram of each of the images, and performs calculations of evaluation values C2.

Figure 8:
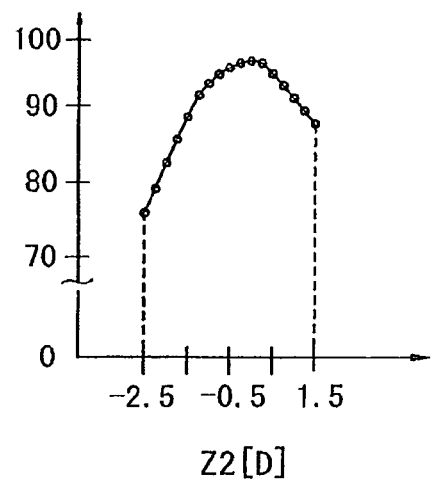
FIG. 8 is a graph which presents a relation between evaluation values C2 of image-formation states and travel positions Z2.

FIG. 8 is a graph which presents a relation between the evaluation values C2 and travel positions Z2 of the focusing lens 24. In FIG. 8, the relation is presented such that the focusing lens 24 is moved in steps of 0.25 D with reference to a position corresponding to −0.5 D which is obtained as the focus position of the SLO optical system 300 within a predetermined range (e.g., a range of ±2.0 D), and the evaluation values C2 are obtained in sequence.

When the evaluation values C2 at the travel positions are obtained as described above, characteristics of the travel positions Z2 and the evaluation values C2 which are obtained discretely are subjected to interpolation to obtain the information on the focus position of the OCT optical system 200. For example, curve approximation is applied to the characteristics using such a function as have its maximum value in a moving range of the focusing lens 24, and a travel position Z2 where the maximum evaluation value C2 is obtained in that curved line is obtained as the focus position. Examples of the manner of detecting the focus position of the OCT optical system 200 by using interpolation as described above include a manner using functional approximation, a manner using calculation of a barycenter, and a manner using calculation of an average value.

Next, the calculation and control unit 70 drives and controls the driving unit 24a to move the focusing lens 24 to a travel position corresponding to the thus-obtained focus position of the OCT optical system 200, whereby the focus adjustment with respect to the OCT fundus image is completed.

Figure 9:
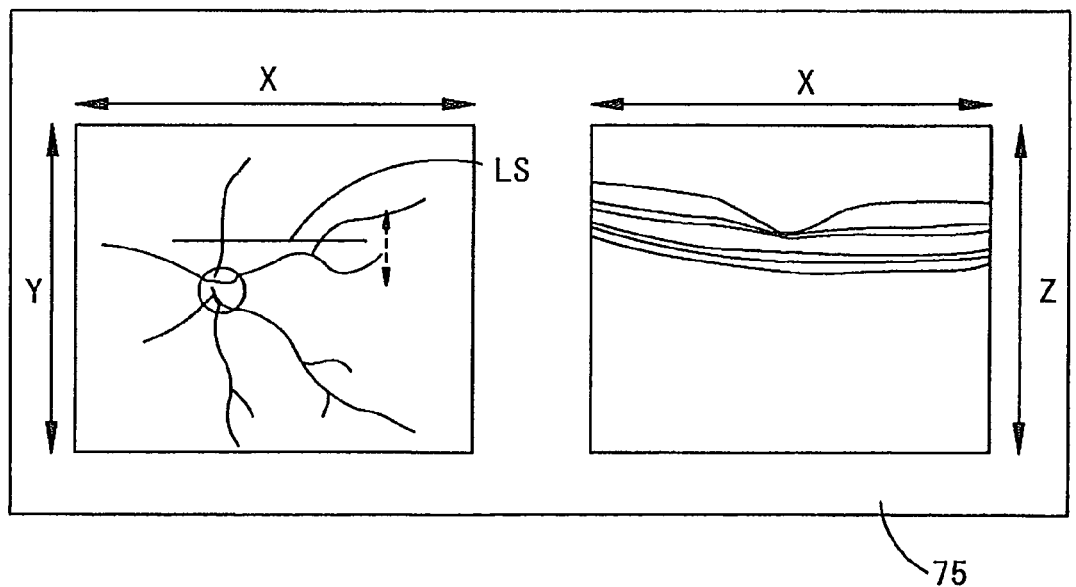
FIG. 9 is a view showing the OCT fundus image and the SLO fundus image, which are displayed side by side on the monitor.

At this time, when the OCT fundus image and the SLO fundus image which are displayed on one screen are brought into appropriate focus as shown in FIG. 9, the examiner sets a position at which the examiner desires to photograph a tomographic image in the SLO fundus image of the SLO image displayed on the monitor 75 which is observed in real time. The examiner manipulates the measurement position setting switch 74b to move a line LS with respect to the SLO fundus image, the line LS indicating a measurement position (an obtainment position) and electrically displayed on the SLO fundus image of the SLO image on the screen, and sets the measurement position. Then, based on the set measurement position, the calculation and control unit 70 performs the photographing operation of the tomographic image on the X-Z plane by the B-scan. Thus, the tomographic image which the examiner desires to photograph is displayed on the monitor 75, and the desired tomographic image and the front image are stored in the memory 72 when the photographing starting switch 74c is pushed by the examiner.

With the above-described configuration, the fundus-photographing apparatus can be provided which is simple in structure, and is capable of performing appropriate focus adjustment. In the preferred embodiment of the present invention, the fundus-photographing apparatus of multifunctional type comprising the OCT optical system 200 arranged to obtain the tomographic image of the fundus and the SLO optical system 300 arranged to obtain the front image of the fundus is explained as an example; however, the present invention can be applied also to a single apparatus such as a fundus-photographing apparatus which has a configuration similar to the OCT optical system 200 and is arranged to obtain a tomographic image, and a fundus-photographing apparatus which has a configuration similar to the SLO optical system 300 and is arranged to obtain a front image.

It is to be noted that, concerning the autofocus with respect to the SLO fundus image, even in a case where the examinee's eye has a disease at its retina (e.g., a case where there is fundus hemorrhage and a blood vessel is partly covered with blood), the focus position can be appropriately detected by obtaining the focus position from the histogram of the whole image as described above. In addition, even in a case where there is a flare in the SLO fundus image, the influence of the flare is reduced and the focus position can be appropriately detected by determining the focus state based on the maximum luminance value which is equal or exceeds the predetermined threshold value (e.g., 20%).

In addition, it is to be noted that, concerning the autofocus with respect to the OCT fundus image, even in a case where the examinee's eye has a disease at its retina (e.g., a case where there is a macular hole which is a hole made in a central retinal fovea of the eye, and a case where there is blood under the retina), the focus position can be appropriately detected by obtaining the focus position from the histogram of the whole image as described above. In addition, even in a case where there is an artifact (abnormal reflection) in a portion of the OCT fundus image which corresponds to a retinal surface, the influence of the artifact is reduced and the focus position can be appropriately detected by determining the focus state based on the maximum luminance value which is equal or exceeds the predetermined threshold value (e.g., 5%).

In the preferred embodiment of the present invention, the fundus-photographing apparatus is explained as an example; however, the present invention is not limited thereto. The present invention can be applied also to an ophthalmic photographing apparatus if the apparatus is arranged to photograph a predetermined region of an examinee's eye, examples of which include an anterior-segment-photographing apparatus arranged to photograph a tomographic image or a front image of an anterior-segment of an examinee's eye.

Concerning the histogram information which is used in the calculation of the evaluation value of the focus state of the image of the examinee's eye, the histogram information which is obtained based on the edge image obtained after subjecting the fundus image to the differential processing is especially effective in a case where blur in the fundus image changes greatly according to the change in the focus position, and the histogram information which is obtained based on the fundus image which is not subjected to the differential processing is especially effective in a case where brightness in the fundus image changes greatly according to the change in the focus position.

In the above-described preferred embodiment of the present invention, the fundus-photographing apparatus arranged to obtain the focus position information of the SLO optical system 300 based on the front fundus image obtained by the SLO optical system 300, and perform based on the obtained focus position information, the rough adjustment of the focus position of the OCT optical system 200 is explained as an example; however, the present invention is not limited thereto.

To be specific, the present invention can be applied to a fundus-photographing apparatus which comprises a photographing optical system (i.e., an optical system for a fundus camera) arranged to illuminate the whole of a funds of an examinee's eye with infrared light emitted from an infrared light source (e.g., a halogen lamp, LED) and obtain a front fundus image by picking up an image of the fundus formed with reflection light of the infrared light reflected from the fundus preferably with the use of a two-dimensional image-pickup element, and the OCT optical system 200 arranged to obtain the OCT fundus image using the low coherent light source. In this apparatus, information on a focus position of the optical system for a fundus camera is obtained based on the infrared fundus image picked up by the two-dimensional image-pickup element arranged to pick up a front fundus image as in the above described manner of detecting the focus position based on the SLO fundus image. However, the manner is not limited to the above-described manner, and it is essential only that the focus position information of the optical system for a fundus camera should be obtained based on a photo-receiving result which is outputted from a photodetector arranged to photo-receive the reflection light from the fundus. For example, it is preferable that the fundus-photographing apparatus further comprises a projection optical system arranged to project a target for focus (e.g., a split target) onto the fundus, and is arranged such that a target image formed by reflection light from the fundus (i.e., a fundus reflection image) is photo-received on the two-dimensional image-pickup element and based on the photo-receiving result outputted from the two-dimensional image-pickup element, the focus position information is obtained.

In the above-described preferred embodiment of the present invention, the fundus-photographing apparatus is arranged such that the focusing lens 63 and the focusing lens 24 are moved in the respective optical axis directions to perform the focus adjustment; however, the present invention is not limited thereto. It is essential only that focusing optical elements which are capable of adjusting the image-formation states of the optical systems should be used. For example, mirror units may be provided instead, which are each arranged to return a photo-received light bundle using two mirrors and to be moved in the optical axis directions to perform the focus adjustment (see Japanese Patent Application Unexamined Publication No. 2005-279121).

In the above-described preferred embodiment of the present invention, the fundus-photographing apparatus has a configuration such that the focusing optical elements are provided separately in the OCT optical system 200 and the SLO optical system 300; however, the present invention can be also applied to a fundus-photographing apparatus having a configuration such that an OCT optical system and an SLO optical system share a light source, an optical scanning system and other members, and a focusing lens is provided on a common optical path of the OCT optical system and the SLO optical system. In this apparatus, when the shared focusing lens is moved in its optical axis direction, focus states of the OCT optical system and the SLO optical system are changed. Hence, it is preferable that the apparatus controls the focusing lens to move to a focus position of the OCT optical system at the time of obtaining the OCT fundus image, and to move to a focus position of the SLO optical system at the time of obtaining the SLO fundus image.

In addition, in the above-described apparatuses, it is also preferable that the focusing lens 63 is moved based on a focus position specified using the OCT fundus image in order to perform more precise focus adjustment with respect to the SLO fundus image. To be specific, the focusing lens 63 may be moved to a travel position which is obtained by applying a predetermined offset to a travel position of the focusing lens 63 which corresponds to the focus position specified using the OCT fundus image. Besides, the predetermined offset is used for correcting a deviation amount of a focus position deviated from the focus position specified using the OCT fundus image in adjusting the travel position of the focusing lens 63, considering that the surface of retina is brought into focus in the SLO optical system 300 while the inside of retina is brought into focus in the OCT optical system 200.

In the description immediately above, the precise autofocus control is performed based on the OCT fundus image obtained by the OCT optical system 200 in performing the autofocus control with respect to the OCT fundus image; however, it is also preferable that information on the focus position of the interference optical system 200 is obtained by correcting, using a predetermined offset, information on the focus position of the interference optical system 200 which is obtained based on information on the focus position of the SLO optical system 300 by the autofocus control with respect to the SLO fundus image, and the focusing lens 24 disposed in the interference optical system 200 is moved to that focus position.

The manner used in the case of performing the autofocus with respect to the OCT image using the focus position information of the SLO optical system 300 is not limited to the above-described manner. It is also preferable that information on the focus position of the OCT optical system 200 is obtained by correcting, using a predetermined offset, information on the focus position of the OCT optical system 200 which is obtained based on information on the focus position of the SLO optical system 300 by the above-described first autofocus control, and the focusing lens 24 is moved to that focus position.

To be specific, an average value of deviation amounts between the focus positions of the SLO optical system 300 and the focus positions of the OCT optical system 200 is obtained in advance by experiment, and is stored as an offset in the memory 72. Then, the calculation and control unit 70 performs a calculation of the focus position of the OCT optical system 200 which corresponds to the focus position of the SLO optical system 300 at the time of performing the first autofocus control, sets a focus position after correction which is obtained by adding the offset to the calculated focus position as the focus position of the OCT optical system 200, and moves the focusing lens 24 to that focus position. In this case, if the offset obtained by experiment is +0.5 D, and the focus position of the SLO optical system 300 is −2.5 D, the focus position of the OCT optical system 200 is set at −2.0 D.

This manner could be inferior in focus precision to the above-described manner in which the focus adjustment is performed based on the OCT fundus image obtained by the OTC optical system 200; however, this manner is more satisfactory in focus precision than the manner of disposing the focusing lens 24 at the focus position corresponding to the focus position of the SLO optical system 300 because the focus position which is obtained by making the above-described correction on the focus position of the SLO optical system 300 is set as the focus position of the OCT optical system 200.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus comprising:
   a photographing optical system arranged to obtain an image of a given region of an examinee's eye, which comprises:
      a light source arranged to illuminate the given region;
      a focusing optical element provided movable in a direction of an optical axis by a driving mechanism; and
      a photodetector arranged to photo-receive reflection light from the given region; and
   a control unit arranged to control driving of the driving mechanism, and obtain the image based on a signal outputted from the photodetector, wherein
   the control unit is arranged to further
      move the focusing optical element in predetermined steps or continuously to obtain the image at each position,
      calculate frequency distribution of luminance of each of the images to detect a change characteristic of luminance values having frequencies equal or exceeding a predetermined threshold value in the frequency distribution with respect to the position of the focusing optical element, and
      detect a focus position of the focusing optical element based on the change characteristics to move the focusing optical element to a position corresponding to the detected focus position.

2. The ophthalmic photographing apparatus according to claim 1, wherein
   the photographing optical system is arranged to photograph a front image of the given region, and
   the control unit is arranged to obtain the front image based on the signal outputted from the photodetector to calculate the frequency distribution of luminance of each of the front images obtained at the positions, the front images being subjected to differential processing.

3. The ophthalmic photographing apparatus according to claim 1, wherein
   the photographing optical system arranged to photograph a tomographic image of the given region further comprises an optical scanner arranged to scan measurement light emitted from the light source, and is arranged to photo-receive interference light between the measurement light reflected from the eye and reference light by the photodetector, and
   the control unit is arranged to obtain the tomographic image based on the signal outputted from the photodetector to calculate the frequency distribution of luminance of each of the tomographic images obtained at the positions.

4. The ophthalmic photographing apparatus according to claim 1, wherein the control unit is arranged to use a change characteristic of a maximum value of the luminance values having frequencies equal or exceeding the predetermined threshold value as the change characteristic.

5. The ophthalmic photographing apparatus according to claim 1, wherein
   the photographing optical system comprises:
      a first photographing optical system arranged to obtain a front image of a fundus of the eye, the system comprising:
         a first light source;
         a first focusing optical element; and
         a first photodetector, and being arranged to illuminate the fundus with light emitted from the first light source, and photo-receive reflection light from the fundus by the first photodetector; and
      a second photographing optical system arranged to obtain a tomographic image of the fundus, the system comprising:
         a second light source;
         a second focusing optical element;
         a second photodetector;
         an optical scanner arranged to scan measurement light emitted from the second light source; and
         an optical-path-length variable optical element, and being arranged to photo-receive interference light between the measurement light reflected from the fundus and reference light by the second photodetector, and the control unit is arranged to obtain the front image of the fundus based on a signal outputted from the first photodetector, and obtain the tomographic image of the fundus based on a signal outputted from the second photodetector, wherein the control unit is arranged to further obtain information on a focus position of the first photographing optical system based on the signal outputted from the first photodetector to move the first focusing optical element to the focus position, and move the second focusing optical element based on the focus position information of the first photographing optical system, and after that further move the second focusing optical element in predetermined steps or continuously to obtain the tomographic image at each position, calculate frequency distribution of luminance of each of the tomographic images to detect a change characteristic of the frequency distribution with respect to the position of the second focusing optical element, and detect a focus position of the second focusing optical element based on the change characteristics to move the second focusing optical element to a position corresponding to the detected focus position.

6. The ophthalmic photographing apparatus according to claim 5, wherein the control unit is arranged to further, after the second focusing optical element is moved based on the focus position information of the first photographing optical system, adjust automatically an optical path length by moving the optical-path-length variable optical element based on the tomographic image, and after that, move the second focusing optical element to the focus position.

* * * * *